United States Patent [19]
Johlin, Jr.

[11] Patent Number: 5,876,450
[45] Date of Patent: Mar. 2, 1999

[54] STENT FOR DRAINING THE PANCREATIC AND BILIARY DUCTS AND INSTRUMENTATION FOR THE PLACEMENT THEREOF

[76] Inventor: Frederick C. Johlin, Jr., 3517 Galway Ct., Iowa City, Iowa 52246

[21] Appl. No.: 853,807

[22] Filed: May 9, 1997

[51] Int. Cl.⁶ .................................. A61F 2/06; A61F 2/04
[52] U.S. Cl. .................................. 623/12; 623/1; 606/194; 606/195
[58] Field of Search .......................... 623/12, 1; 606/154, 606/194, 195, 198, 191, 108, 109

[56] References Cited

U.S. PATENT DOCUMENTS

| | | | |
|---|---|---|---|
| 4,441,495 | 4/1984 | Hicswa ..................................... | 128/325 |
| 4,531,933 | 7/1985 | Norton et al. ............................. | 604/8 |
| 5,282,784 | 2/1994 | Willard ..................................... | 604/8 |
| 5,401,257 | 3/1995 | Chevalier, Jr. et al. ................. | 606/195 |
| 5,429,605 | 7/1995 | Richling-Bernd et al. ............. | 606/194 |
| 5,474,563 | 12/1995 | Myler et al. ............................. | 606/108 |
| 5,522,883 | 6/1996 | Slater et al. .............................. | 623/1 |
| 5,545,209 | 8/1996 | Roberts et al. ........................... | 623/1 |
| 5,562,641 | 10/1996 | Flomenblit et al. ..................... | 606/198 |
| 5,569,201 | 10/1996 | Burns ........................................ | 606/194 |

OTHER PUBLICATIONS

*Removable Biliary Endoprosthesis*, Technical Notes, Julio C. Palmaz and Eugene J. Burbige, Apr. 1983.
*Large–Bore, Long Biliary Endoprostheses (Biliary Stents) for Improved Drainage*, Harold G. Coons, M. D., Patrick H. Carey, M. D.; Radiology, vol. 148, No. 1, pp.89–94, Jul., 1989.

*Primary Examiner*—Mickey Yu
*Assistant Examiner*—Suzette J. Jackson
*Attorney, Agent, or Firm*—Woodard, Emhardt, Naughton, Moriarty & McNett

[57] ABSTRACT

A stent is disclosed for placement within the pancreatic or biliary duct to facilitate drainage therethough, and related instrumentation which facilitates the atraumatic placement of the stent within the duct. The stent is atraumatically placed by means of an instrumentation system which draws or pulls the stent into position and wedges the distal end portion of the stent into the terminating portion of the duct to maintain the stent in place within the duct. As described herein, the stent is made of a soft biocompatible material which is resiliently compliant so as to allow the stent to readily conform to the curvature of the ductal passageway in which it has been placed. When placed, the stent extends along the length of the duct, with the proximal end extending into the duodenum. Perforations in the stent further faciliate drainage along the length of the stent.

1 Claim, 5 Drawing Sheets

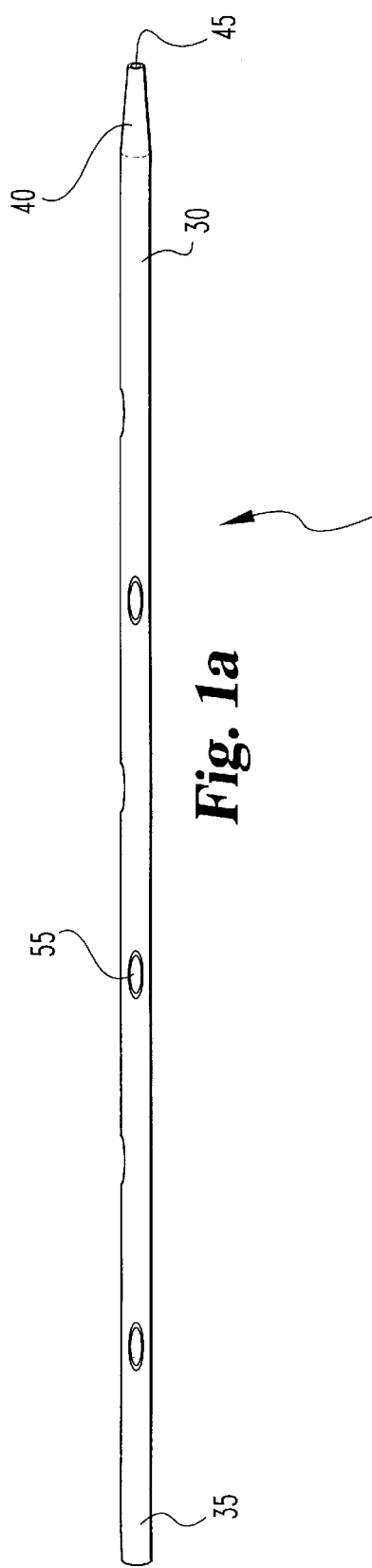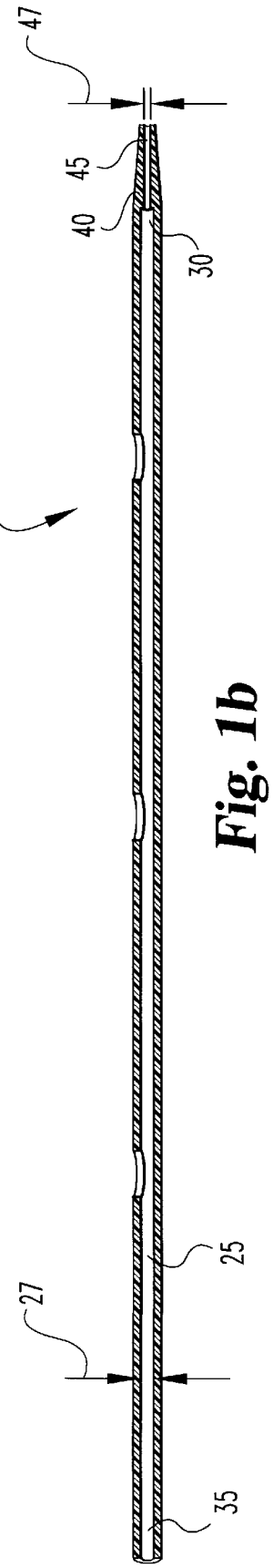

STENT FOR DRAINING THE PANCREATIC AND BILIARY DUCTS AND INSTRUMENTATION FOR THE PLACEMENT THEREOF

FIELD OF THE INVENTION

The present invention relates to the field of stents and stent systems for the drainage of fluids from the biliary and pancreatic ducts.

BACKGROUND OF THE INVENTION

Where a biliary or pancreatic duct becomes occluded, it is often desirable to facilitate drainage through the duct by the placement of a stent within the occluded area. Conventional stents for this purpose are commonly made of polyethelene and teflon and include flaps or barbs at each end of the stent which serve to prevent migration and retain the stent in place. Stents have also been commonly pre-formed at their ends into various retaining configurations, such as pigtails or spirals, to help maintain the stent in position. Stents have also been formed into various expandable configurations so that, when the stent has reached the occluded area, the stent is expanded to press outwardly against the ductal wall and to thereby maintain its position within the duct. Biliary and pancreatic stents are typically pushed into place by a "pusher" catheter which is advanced from behind the stent and pushes against the proximal end of the stent until the stent has reached its desired location.

During the placement procedure, conventional retaining elements have been known to have an abrasive effect on the surrounding ductal tissue as they pass through the duct, thus causing or aggravating inflamation of the duct. Conventional retaining elements have also been known to cause aggravation to the ductal tissue while the stent is left in place, and particularly, when the stent is removed.

There is a need for an improved stent which can be atraumatically placed within an occluded biliary or pancreatic duct and maintained in place without causing aggravation to the ductal tissue, and which further can be removed without damaging the duct. There is also a further need for improved instrumentation for facilitating the atraumatic placement of a stent within a biliary/pancreatic duct.

SUMMARY OF THE INVENTION

The present invention provides a new and improved stent which is particularly useful for placement within the pancreatic or biliary duct to facilitate drainage therethough, and related instrumentation which facilitates the atraumatic placement of the stent within the duct. The stent is placed and maintained in position within the duct without barbs or other retaining elements which can cause damage to the ductal tissue. The stent is atraumatically placed by means of a unique instrumentation system which draws or pulls the stent into position and wedges the distal end portion of the stent into the terminating portion of the duct to maintain the stent in place within the duct. As described herein, the stent is made of a soft biocompatible material which is resiliently compliant so as to allow the stent to readily conform to the curvature of the ductal passageway in which it has been placed. When placed, the stent extends along the length of the duct, with the proximal end extending into the duodenum. Peforations in the stent further faciliate drainage along the length of the stent.

It is an object of this invention to provide a stent which can be atraumatically placed and maintained within a biliary or pancreatic duct.

It is another object of this invention to provide instrumentation for atraumatically placing a stent within a biliary or pancreatic duct.

It is still a further object of this invention to provide a biliary/pancreatic stent which will not irritate or cause inflammation to the ductal walls while the stent is left in place.

A further object of this invention is to provide a stent which is retained in place without the use of barbs, flaps, pigtails, spirals or by expansion of the stent against the walls of the duct.

It is a further object of this invention to provide a biliary/pancreatic stent which can be reliably maintained in position when placed within the duct and which can be readily removed without causing damage to the ductal tissue.

Further objects, features and advantages of the present invention shall become apparent from the detailed drawings and descriptions provided herein.

BRIEF DESCRIPTION OF THE DRAWINGS

FIGS. 1*a* and 1*b* are views of a pancreatic/biliary stent 20 according to the present invention. FIG. 1*a* is a side elevational view of stent 20. FIG. 1*b* is a longitudinal cross-sectional view of stent 20.

DETAILED DESCRIPTION OF THE PREFERRED EMBODIMENT

Figure 2:
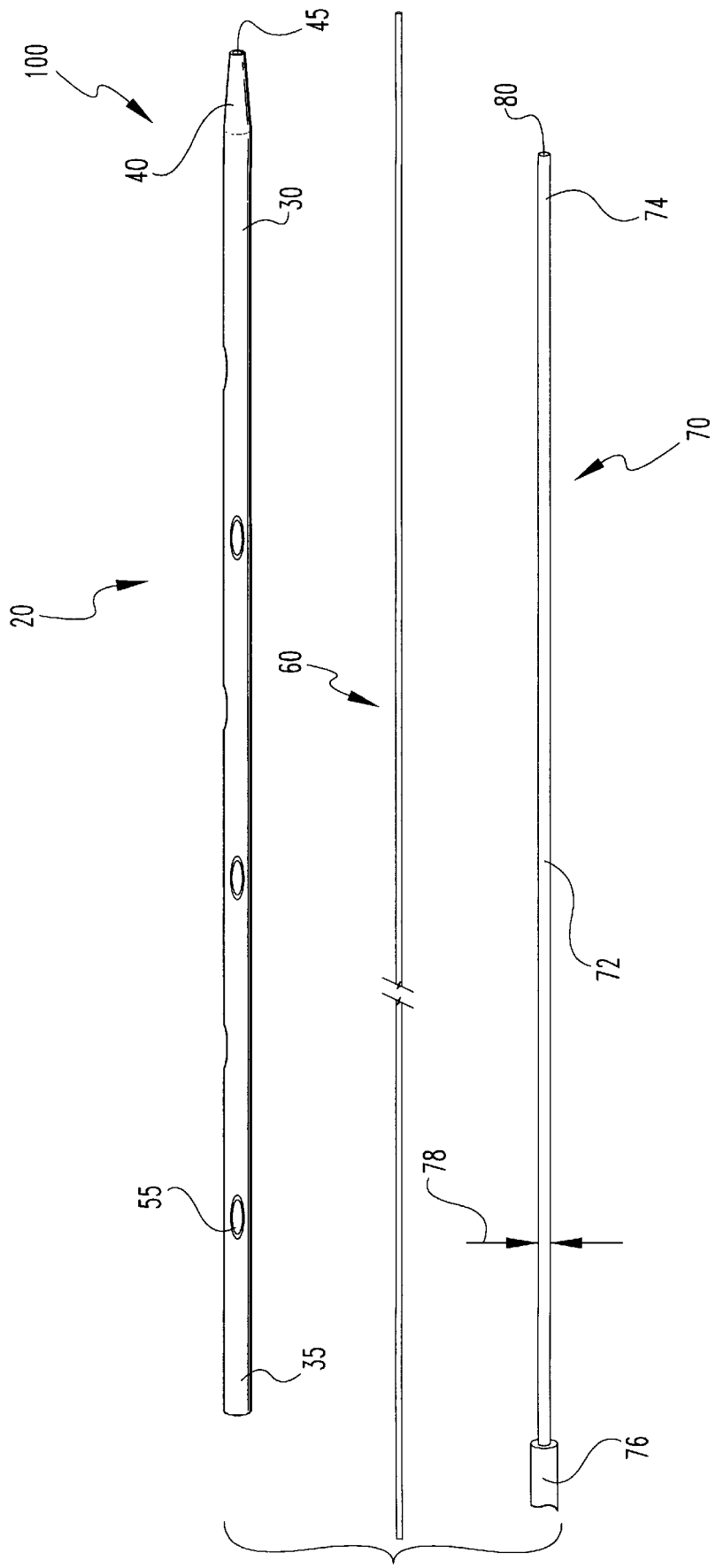
FIG. 2 is a partial perspective view of a stent introduction system according to the present invention, including stent 20, wire guide 60, and introducer catheter 70.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and further modifications in the described device, and any further applications of the principles of the invention as described herein are contemplated as would normally occur to one skilled in the art to which the invention relates. The drawings show relative sizes only; measurements and positions are exaggerated for purposes of illustration.

According to the following described preferred embodiment, stent 20 is provided which is made of a soft biocompatible material that is resiliantly compliant and is sized and shaped to "wedge" into the terminal portion of a biliary or pancreatic duct with the stent extending the length of the duct and with its proximal end extending into the duodenum. Stent introduction system 100 is used to securely deploy stent 20 into its desired location within the duct, with the distal end portion of stent 20 being pressed or wedged into the terminal portion of the duct.

Referring first to FIGS. 1a and 1b, stent 20 has a basically tubular shape and is made of a soft biocompatible material with a smooth and continuous outer surface. The material should preferably be selected to be resiliently compliant so as to readily conform to the curvature of the duct in which it is to be placed, while having sufficient "hoop" strength to retain its form within the duct. In the preferred embodiment, stent 20 is made from Silastic® silicon rubber made by Dow Corning Corp. Alternatively, other biocompatible materials may prove satisfactory as well. Also, it is contemplated that stent 20 may be constructed to be radiopaque, as is known in the art, and also may be made of various composite materials as well. For instance, stent 20 could be lined with a thin layer of metal, such as silver or gold, to prevent bio-film formation while the stent is left in place within the patient.

Stent 20, which is presented for placement within the pancreatic duct, has a distal end portion 30, a proximal end portion 35, and defines internal lumens 25 and 45 extending therethrough. When stent 20 is to be placed, distal end portion 30 enters the patient first and is to be deployed into the tail end or terminus of the pancreatic duct. Internal lumen 25 has an inner diameter 27 sized to receive an introducer catheter and a wire guide (described below). When placed, stent 20 extends along the full length of the pancreatic duct in which it has been placed, with proximal end portion 35 extending into the duodenum of the patient.

Distal end portion 30 of stent 20 is formed into a conical or tapered shape at its terminating end. Tapered section 40 defines an inner wire guide lumen 45 with a diameter 47 smaller than inner diameter 27 of central lumen 25, thereby defining an interior shoulder at the juncture between central lumen 25 and wire guide lumen 45. Stent 20 has perforations 55 along its length to enhance the flow of fluids through the duct.

Figure 3:
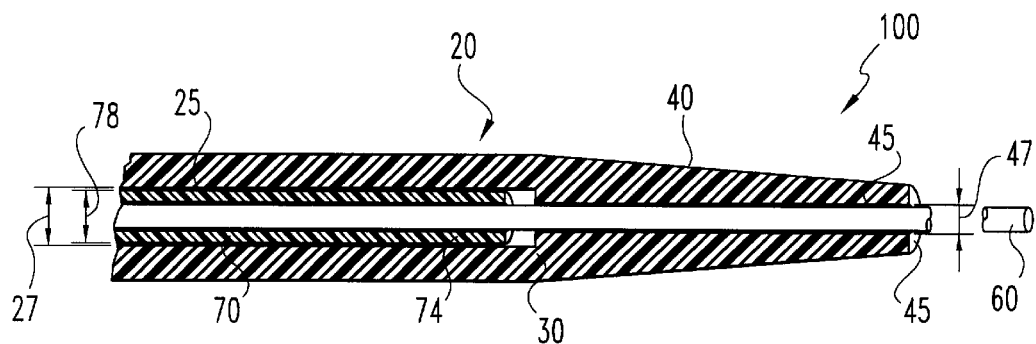
FIG. 3 is a partial, enlarged view of the distal end of stent 20, with wire guide 60 placed therethrough and with the distal end portion of introducer catheter 70 placed within the central lumen of stent 20.

FIGS. 2 and 3 illustrate stent introduction system 100. Stent 20, wire guide 60 and introducer catheter 70 are shown according to a preferred embodiment of the invention. Wire guide 60 is a stiff endoscopic access wire guide that is 0.035" in diameter. Lumens 25 and 45 of stent 20 (discussed above) have inner diameters 27 and 47 respectively, greater than the diameter of wire guide 60. Introducer catheter 70 has a generally tubular shape with distal portion 72, including distal end 74, and proximal portion 76. Introducer catheter 70 defines an inner lumen 80 with a diameter sized to slide freely over wire guide 60. Distal portion 72 of introducer catheter 70 has an outer diameter 78 which is less than inner diameter 27 of lumen 25 of stent 20 and which is greater than diameter 47 of lumen 45 of tapered section 40. Once stent 20 has been deployed on wire guide 60, with distal end 30 towards the patient, introducer catheter 70 is advanced along wire guide 60 and distal end 76 of introducer catheter 70 enters proximal end 35 of stent 20. Distal portion 72 of introducer catheter 70 slides past proximal end 35 of stent 20 along wire guide 60 and continues until distal end 74 of introducer catheter 70 reaches and abuts the interior shoulder at the distal end portion 30 of stent 20. In a preferred embodiment, proximal portion 76 of introducer catheter 70 has a diameter greater than diameter 78 of distal portion 72. Wire guide 60 and catheter 70 have lengths sufficient to extend from the desired location in the patient's body to outside the body, as normally understood in the art.

Figure 4:
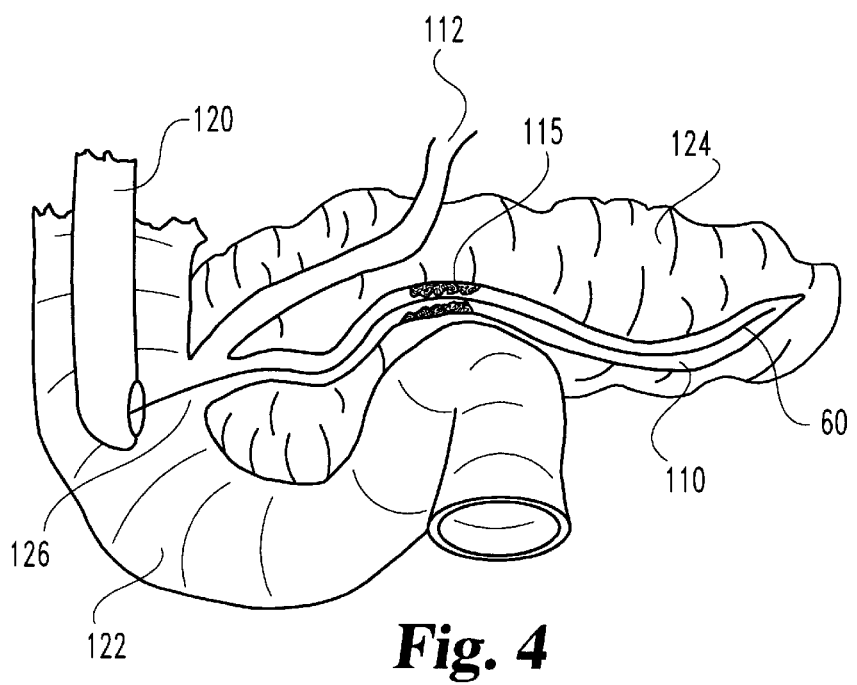
FIG. 4 is a diagrammatic view of wire guide 60 advanced through the occluded area of a pancreatic duct and to the terminus of the duct.

Referring now to FIGS. 4–7, a method for using stent introduction system 100 is illustrated. FIG. 4 illustrates duodenum 122 and pancreas 124 with pancreatic duct 110 and biliary duct 112, with occlusion 115 in pancreatic duct 110. Pancreatic duct 110 and biliary duct 112 branch off from duodenum 122 through common bile duct 126. Duct 110 is understood to have various bends and turns varying with each patient. Wire guide 60 is advanced into the patient, through an endoscope 120 which has been advanced into the duodenum 122, and wire guide 60 is further advanced into duct 110 and past occlusion 115 to the terminating end of duct 110. Stent 20 and introducer catheter 70 are then deployed on wire guide 60 outside of the patient and advanced over wire guide 60 into the patient and to duct 110.

Figure 5:
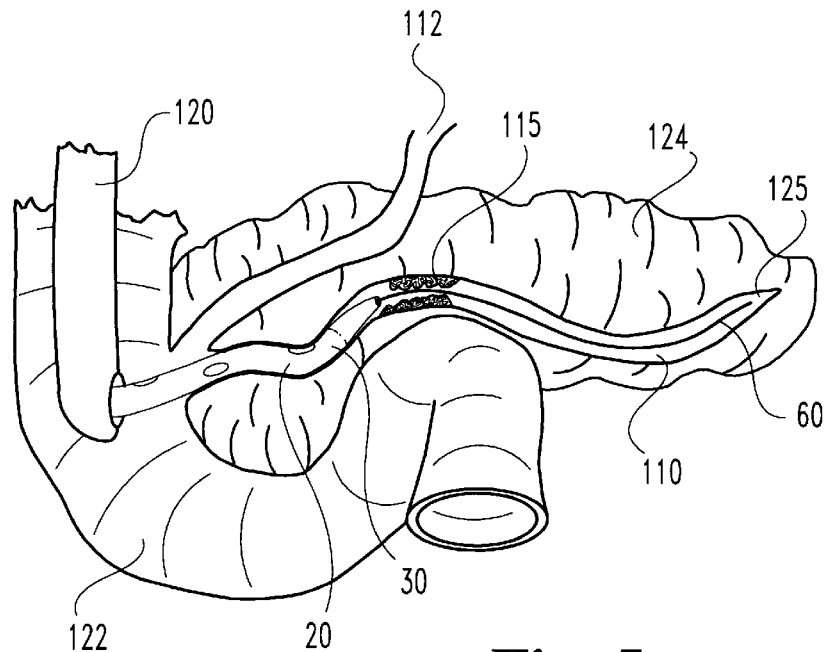
FIG. 5 is a diagrammatic view of stent 20 being advanced to an occluded duct over wire guide 60.
Figure 6:
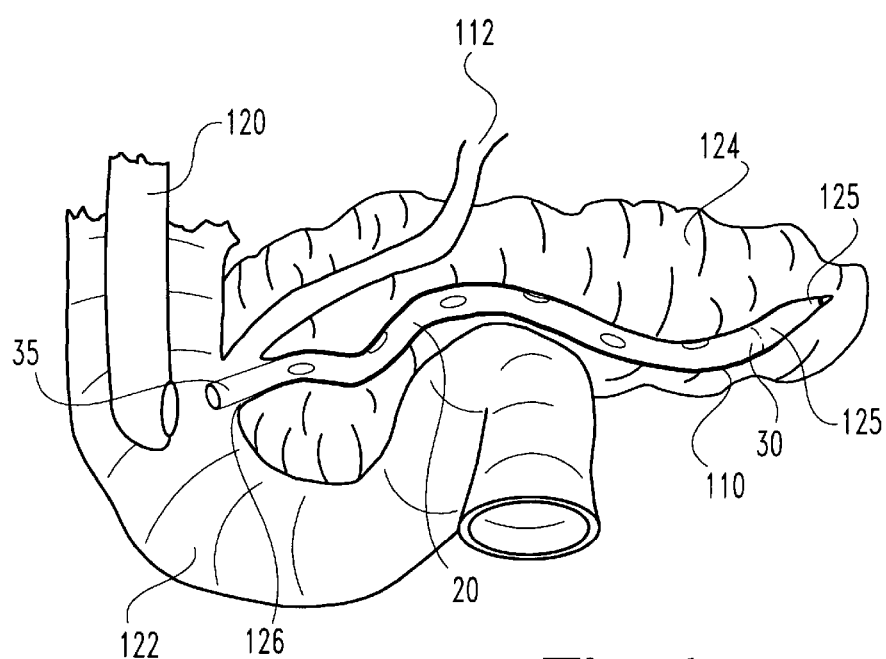
FIG. 6 is a diagrammatic view of stent 20 deployed within a pancreatic duct
Figure 7:
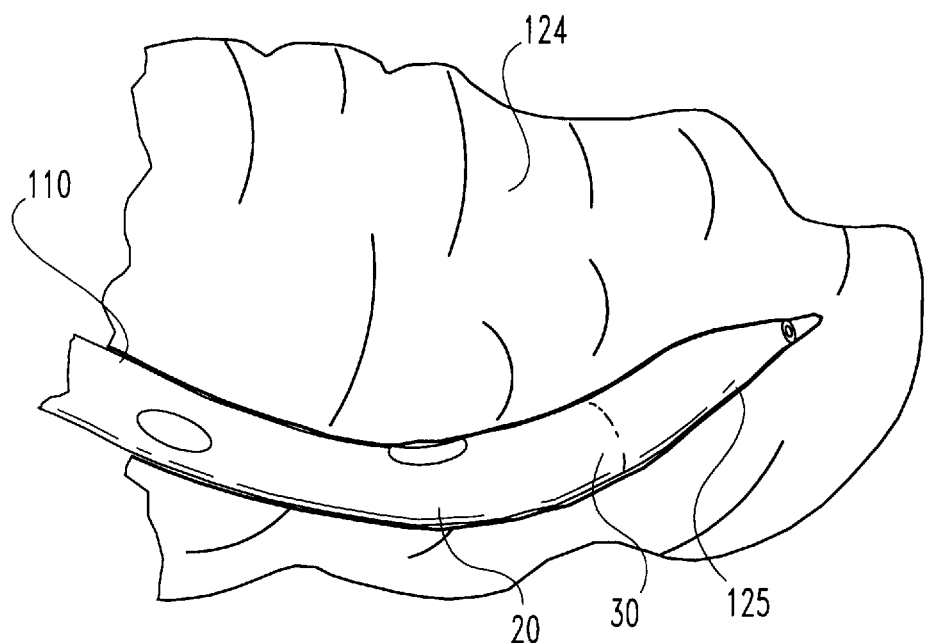
FIG. 7 is an enlarged diagrammatic view showing stent 20 wedged into position at the terminal portion of the pancreatic duct.

As shown in FIGS. 5 and 6, introducer catheter 70 is advanced through endoscope 120 along wire guide 60 to lead stent 20 towards and past occlusion 115 by pressing against the interior shoulder at the distal end portion 30 of stent 20. Stent 20 and introducer catheter 70 are advanced until distal end portion 30 of stent 20 reaches the terminal end 125 of duct 110. The outer diameter of stent 20 is sized to be approximately the size of the diameter of duct 110 in its normal unoccluded state. As illustrated in FIG. 7, distal end portion 30 of stent 20 may then be "wedged" into the terminal end 125 of duct 110 to form a compression fit therein. Stent 20 has a length that at least extends the length of duct 110. The length of stent 20 may be pre-sized or can be measured and trimmed to a size after a measurement of the length of the duct has been taken. Proximal end 35 remains outside of duct 110 and common bile duct 126 and extends into the duodenum. Since stent 20 is made from compliant material, it will conform to the various bends and twists in the duct passageway. Once stent 20 has been successfully emplaced, wire guide 60 and introducer catheter 70 are withdrawn leaving stent 20 in duct 110. Stent 20 will then remain in duct 110 without abrasion or irritation to the surrounding ductal tissue.

Once stent 20 is in place, it maintains the patency of duct 110, allowing fluid to flow through internal lumen 25 towards proximal end 35. As noted above, the material for stent 20 should be selected to have sufficient hoop strength so as not to collapse in response to radial compressive forces acting upon by duct 110. Stent 20 also has radially placed perforations 55 along its length which further enhance the flow of bile or fluid through stent 20 by allowing fluid to enter at various places along the length of stent 20.

When stent 20 is to be removed from duct 110, the proximal portion of stent 20 extending into the duodenum may be simply grasped by a retractor, snare, or other instrument and pulled out of the duct. Without barbs, flaps, preformed shapes or expanded portions which could potentially abraid the ductal tissue, stent 20 is atraumatically removed without causing harm to the duct.

As noted above, the size and length of stent 20 should be selected relative to the size and length of the duct in which it is to be placed. By illustration, stent 20 may be formed to have an 8 Fr outer diameter with a 5 Fr interior central lumen. Stent 20 is tapered along its distal 8 mm to a terminating diameter of 5 Fr, with a wire guide lumen therein sized to receive a 0.035 wire guide. As noted, stent 20 is preferably sized to be at least as long and slightly longer than the length of a duct from the duodenum to the terminus or "tail" of the duct. For instance, for a pancreatic duct measuring a length of 16 cm, a stent of 16.5 cm may be used.

An introducer catheter 70 corresponding to the above dimensioned stent 20, for instance, may be sized to have an outer diameter of 7 Fr at its proximal portion 76. The distal portion 72 of introducer catheter 70 is corresponding sized to a 4.5 Fr thin walled section with a forward end which abuts the interior shoulder of stent 20 and is advanced to pull or draw stent 20 into position. Introducer catheter 70 should preferably be made of urethane or another material with sufficient rigidity to be guided, but which is sufficiently flexible to be introduced through an endoscope and along wire guide 60 to the duodenum. The distal portion 72 of introducer catheter 70, which enters stent 20 and has a reduced diameter sized to be received within central lumen of stent 20, is preferably made of a relatively more rigid, but flexible, material such as baked urethane. Other materials which have sufficient axial rigidity to direct stent 20 into place, but which are also sufficiently flexible to be guided through the duct may also be suitable. For instance, nitinol or another superelastic alloy may be suitable for this purpose.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A stent for placement in a desired duct in a patient, the duct including a proximal end and a terminating distal end portion, and an introduction system for the placement of said stent into the desired duct, comprising:

a wire guide, said wire guide being sized and shaped for advancement to the terminating distal end portion of the duct;

a stent made of a biocompatible material, said stent being formed in a generally tubular shape and having a proximal end portion with an open proximal end thereat, and an distal end portion with an open distal end thereat, and having an internal lumen with an inner diameter greater than the diameter of said wire guide; said internal lumen extending along the length of said stent from said open proximal end to said open distal end, said stent being deployable onto said wire guide with said distal end of said stent towards the duct and with said wire guide passing through said internal lumen of said stent; said stent further defining an interior shoulder within the distal end portion thereof; and an introducer catheter, said introducer catheter defining an inner lumen therethrough sized to receive said wire guide, said introducer catheter having a distal end portion with a terminating distal end thereof, said distal end portion of said introducer catheter being sized to be received into the internal lumen of said stent with the terminating distal end thereof abutting against the interior shoulder within the distal end portion of said stent; and wherein said introducer catheter is advanceable to press the terminating distal end thereof against the interior shoulder of the distal end portion of said stent and to thereby wedge the distal end portion of said stent into the terminating distal end portion of the duct, and whereby the stable placement of said stent into the duct is effectively accomplished.

\* \* \* \* \*